(12) United States Patent
Maeda et al.

(10) Patent No.: US 8,707,761 B2
(45) Date of Patent: Apr. 29, 2014

(54) PARTICULATE MATTER DETECTION ELEMENT

(75) Inventors: Eriko Maeda, Okazaki (JP); Takehito Kimata, Kariya (JP); Yushi Fukuda, Aichi-ken (JP)

(73) Assignee: Denso Corporation, Kariya (JP)

( * ) Notice: Subject to any disclaimer, the term of this patent is extended or adjusted under 35 U.S.C. 154(b) by 230 days.

(21) Appl. No.: 13/282,687

(22) Filed: Oct. 27, 2011

(65) Prior Publication Data

US 2012/0103058 A1    May 3, 2012

(30) Foreign Application Priority Data

Oct. 28, 2010   (JP) ................................ 2010-242189

(51) Int. Cl.
     *G01N 37/00*      (2006.01)
     *G01N 7/00*      (2006.01)

(52) U.S. Cl.
     USPC ........................................ 73/28.01; 73/23.33

(58) Field of Classification Search
     USPC ............................................. 73/23.33, 28.01
     See application file for complete search history.

(56) References Cited

U.S. PATENT DOCUMENTS

| | | | | |
|---|---|---|---|---|
| 2008/0264146 A1* | 10/2008 | Roesch et al. | ............... | 73/23.33 |
| 2009/0051376 A1 | 2/2009 | Schnell et al. | | |
| 2012/0047991 A1 | 3/2012 | Tokuda et al. | | |
| 2012/0047993 A1 | 3/2012 | Tokuda et al. | | |

FOREIGN PATENT DOCUMENTS

| | | |
|---|---|---|
| JP | 59-197847 | 11/1984 |
| JP | 9-185038 | 7/1997 |
| JP | 2008-502892 | 1/2008 |
| JP | 2009-045604 | 3/2009 |
| JP | P2012-047596 A | 3/2012 |
| JP | P2012-047597 A | 3/2012 |

OTHER PUBLICATIONS

Japanese Official Action dated Oct. 9, 2012 issued in corresponding Japanese Application No. 2010-242189, with English translation.

* cited by examiner

*Primary Examiner* — Hezron E Williams
*Assistant Examiner* — David Z Huang
(74) *Attorney, Agent, or Firm* — Nixon & Vanderhye P.C.

(57) ABSTRACT

A shielding part is formed on a detection part in a particulate matter detection element. The detection part has a pair of detection electrodes formed in a comb structure. A shielding layer is made of heat insulating material and formed on the detection part in order to shield a predetermined area having non-uniform electric field intensity. An area having uniform electric field intensity on the detection part is exposed only to exhaust gas as target detection gas when a predetermined voltage is supplied between the detection electrodes in order to detect electric characteristics of the detection part. This structure prevents the area other than the area having the uniform electric field intensity on the detection part from being exposed to the exhaust gas.

2 Claims, 8 Drawing Sheets

PARTICULATE MATTER DETECTION ELEMENT

CROSS-REFERENCE TO RELATED APPLICATION

This application is related to and claims priority from Japanese Patent Application No. 2010-242189 filed on Oct. 28, 2010, the contents of which are hereby incorporated by reference.

BACKGROUND OF THE INVENTION

1. Field of the Invention

The present invention relates to particulate matter detection elements used to an exhaust gas purifying system for an internal combustion engine of a motor vehicle, and are capable of detecting particulate matter contained in target detection gas such as exhaust gas emitted from the internal combustion engine.

2. Description of the Related Art

The present invention relates to particulate matter detection sensors mounted to an exhaust gas purifying system for an internal combustion engine of a motor vehicle and capable of detecting particulate matter contained in exhaust gas emitted from the internal combustion engine.

In general, a diesel engine, for example, mounted to a motor vehicle, is equipped with a diesel particulate filter (hereinafter, referred to as the "DPF"). Such a DPF captures particulate matter (hereinafter, referred to as the "PM" for short) as environmental pollution matter contained in exhaust gas emitted from the diesel engine. The PM contains soot and soluble organic fraction (SOF). The DPF is composed of a plurality of cells surrounded by partition walls having a plurality of pores. When the exhaust gas passes through the pores formed in the partition walls, the pores capture PM contained in the exhaust gas. The exhaust gas is thereby purified.

When a quantity of PM captured in the pores formed in the partition walls in the DPF is increased, the pores are clogged and a pressure loss of the DPF is thereby increased. In order to avoid this and to regenerate the capturing function of the DPF, it is necessary to periodically execute a process of regenerating the DPF.

In general, the regeneration cycle of the DPF is determined on the basis of detecting a quantity of PM captured in the DPF. It is therefore necessary to place a pressure sensor capable of detecting a difference between a pressure at a upstream side and a pressure at a downstream side of the DPF. The regeneration process heats the exhaust gas or executes a post injection in order to heat the exhaust gas, and introduces the heated exhaust gas into the inside of the DPF. This removes PM captured in the pores formed in the partition walls of the DPF.

On the other hand, there have been proposed various types of particulate matter detection sensors (hereinafter, referred to as the "PM detection sensor") capable of directly detecting the presence of PM contained in exhaust gas. For example, such a PM sensor is placed at the downstream side of the DPF, and detects a quantity of PM contained in the exhaust gas passing through the DPF. An on-board diagnosis mounted to a motor vehicle monitors the output of the PM sensor in order to detect the working condition of the DPF, and occurrence of defects and damage of the DPF.

It has also been proposed to place such a PM sensor, instead of using a pressure difference sensor, at the upstream of the DPF, and to detect a quantity of exhaust gas introduced into the DPF. This can determine the optimum time of regenerating the DPF on the basis of the detected quantity of PM.

A conventional patent document 1, a Japanese patent laid open publication No. S59-197847, has disclosed a smoke sensor of an electrical resistance type as one example of the above PM sensor. The smoke sensor is comprised of an insulation substrate, a pair of conductive electrodes as a detection part, and a heating unit. The pair of conductive electrodes is formed on one surface of the insulation substrate, and the heating unit is formed in the inside or the bottom surface of the insulation substrate.

The smoke sensor detects the presence of smoke (particulate carbon) in exhaust gas on the basis of using electrical conductivity of the smoke. The smoke sensor detects the change of a resistance value between the conductive electrodes, which is changed according to the quantity of smoke accumulated on the area between the conductive electrodes.

The heating unit generates heat energy when receiving electric power. The heat energy increases a temperature of the PM detection part to a desired temperature (for example, a temperature within a range of 400° C. to 600° C.), and burns the smoke accumulated on the area between the conductive electrodes. This makes it possible to recover the detection capability of the smoke sensor.

In such a type of the PM detection sensor, the surface of the substrate other than the detection part is covered with an airtight insulation substrate in order to prevent a conductive path from being generated by PM accumulation on the surface of the part other than the detection part, and to prevent incorrect operation from thereby occurring. (For example, FIG. 1 shown in the patent document 1).

Further, such a type of the PM detection sensor has a large resistance value between detection electrodes until a predetermined quantity of PM is accumulated on the area between the detection electrodes on the detection part. In particular, there is known a dead time period (mass) during which the PM detection sensor outputs no detection signal.

In another (Japanese) conventional patent document 2, Kohyo (National publication of translated version) No. JP 2008-502892, discloses a conventional technique capable of changing a voltage supplied to the detection electrodes formed in a comb structure, and of increasing the supplied voltage at a detection initial period in order to increase an electric field intensity generated between the detection electrodes. This promotes a PM accumulation speed accumulated on the area between the detection electrodes, and decreases the dead time period. After completion of the dead time period, the conventional technique decreases the supply voltage in order to decrease the electric field intensity between the detection electrodes. This makes it possible to decrease the PM accumulating speed and to extend the period to start a process of regenerating the PM detection sensor.

By the way, when the PM accumulating speed is promoted by supplying a high voltage between a pair of the detection electrodes formed in a comb structure in which electrodes arranged opposite together, for example, as disclosed in the conventional patent document 2, a front part of each detection electrode has a high electric field intensity because of concentrating the electric field. On the other hand, the bottom part of each detection electrode has a low electric field intensity, which is connected to a corresponding detection electrode lead part and connected in a direction which is perpendicular to the corresponding detection electrode lead part formed along a longitudinal direction of the PM detection sensor.

When there is an area having a non-uniform distribution of electric field intensity (or non-uniform electric field intensity) on the detection part of the PM detection sensor, the PM accumulating speed is not constant, the quantity of PM accumulated on the detection part is fluctuated, In particular, as shown in the patent document 2, when the supplied voltage is increased in order to increase the quantity of PM accumulated on the detection part, the non-uniform distribution of electric field intensity occurs. In general, PM is more accumulated on the area having a high electric field intensity when compared with the area having a low electric field intensity. This increases a difference between the high electric field intensity and the low electric field intensity, and makes non-uniform distribution of PM accumulated on the detection electrodes. The more the degree of the non-uniform distribution is increased, the more the probability of generating incorrect output from the PM detection sensor is increased. This reduces the reliability of the PM detection sensor.

SUMMARY

It is therefore desired to provide a particulate matter detection element having a stable dead time period with high reliability, capable of detecting a quantity of particulate matter contained in a target detection gas on the basis of a change of electrical characteristics of a pair of detection electrodes with a simple structure. The electrical characteristics of the electrode are changed on the basis of the quantity of particulate matter accumulated on the area between the pair of the detection electrodes with a simple configuration.

To achieve the above purposes, the present exemplary embodiment provides a particulate matter detection element capable of detecting particulate matter contained in a target detection gas. The particulate matter detection element has an insulation substrate, a detection part, and a shielding layer. The detection part has a pair of detection electrodes formed at a predetermined interval on a surface of the insulation substrate. The shielding layer is made of heat insulating material. The shielding layer covers a predetermined area on the detection part so that an area having a uniform electric field intensity generated when a voltage is supplied between the detection electrodes is exposed to the target detection gas. An area other than the area having the uniform electric field intensity is shielded from the target detection gas. That is, the area other than the area having the uniform electric field intensity on the detection part is not exposed to the target detection gas.

In the particulate matter detection element according to the present exemplary embodiment, the area other than the area having the uniform electric field intensity formed on the detection part does not include an area in which equipotential lines of the electric field generated when the voltage is supplied between the detection electrodes are approximately parallel to a reference line defined along a longitudinal part of each of the detection electrodes.

Further, in the particulate matter detection element according to the present exemplary embodiment, an angle of the equipotential line of the electric field in the area other than the area having the uniform electric field intensity to the reference line exceeds ±3°.

The structure of the particulate matter detection element according to the exemplary embodiment makes it possible to prevent particulate matter from being accumulated on the area having non-uniform electric field intensity, and to promote the accumulation of particulate matter on the area having the uniform electric field. This makes it possible to suppress particulate matter from being locally accumulated on the detection part, to make the dead time period constant, to obtain a stable detection output.

For example, when the detection electrode has a width of 150 μm, a distance between the adjacent detection electrodes which face to each other is 50 μm, and a distance from the front part of one detection electrode to the detection electrode lead part corresponding to the other detection electrode is at least 50 μm, the area covered with the shielding area is at least 50 μm measured from the front part of the detection electrode, that is, the distance from the front part of one detection electrode to the detection electrode lead part corresponding to the other detection electrode, or not less than the inter-electrode distance.

BRIEF DESCRIPTION OF THE DRAWINGS

A preferred, non-limiting embodiment of the present invention will be described by way of example with reference to the accompanying drawings, in which.

DETAILED DESCRIPTION OF THE PREFERRED EMBODIMENTS

Figure 1A:
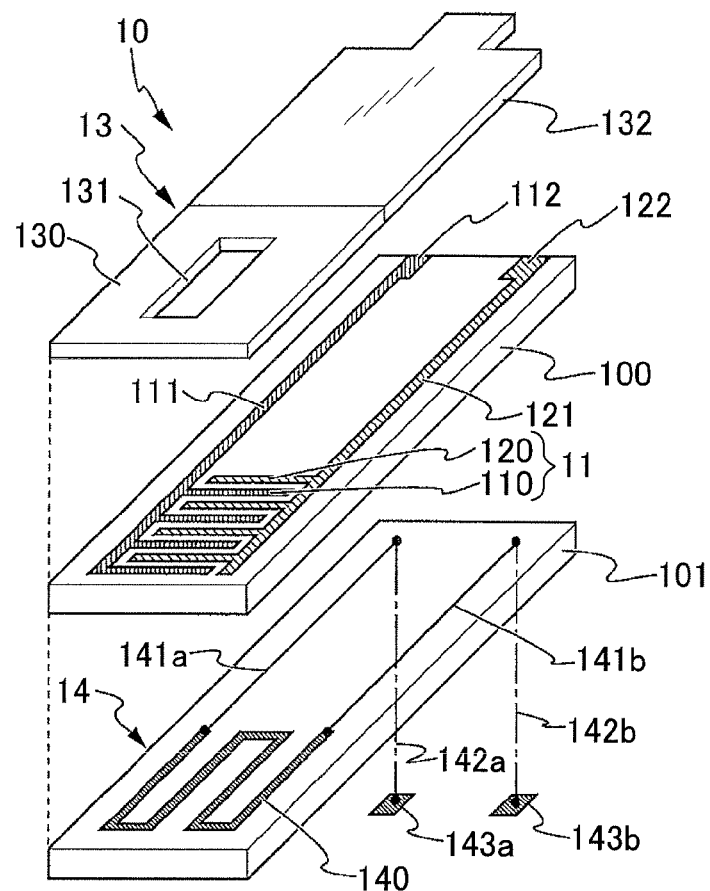
FIG. 1A is a development view showing a perspective structure of a particulate matter (PM) detection element according to a first exemplary embodiment of the present invention.

Hereinafter, various embodiments of the present invention will be described with reference to the accompanying drawings. In the following description of the various embodiments, like reference characters or numerals designate like or equivalent component parts throughout the several diagrams.

First Exemplary Embodiment

A description will be given of a particulate matter detection element 10 (hereinafter, referred to as the "PM detection element 10'') according to a first exemplary embodiment of the present invention with reference to FIG. 1A to FIG. 6F.

Figures 1B, 1C:
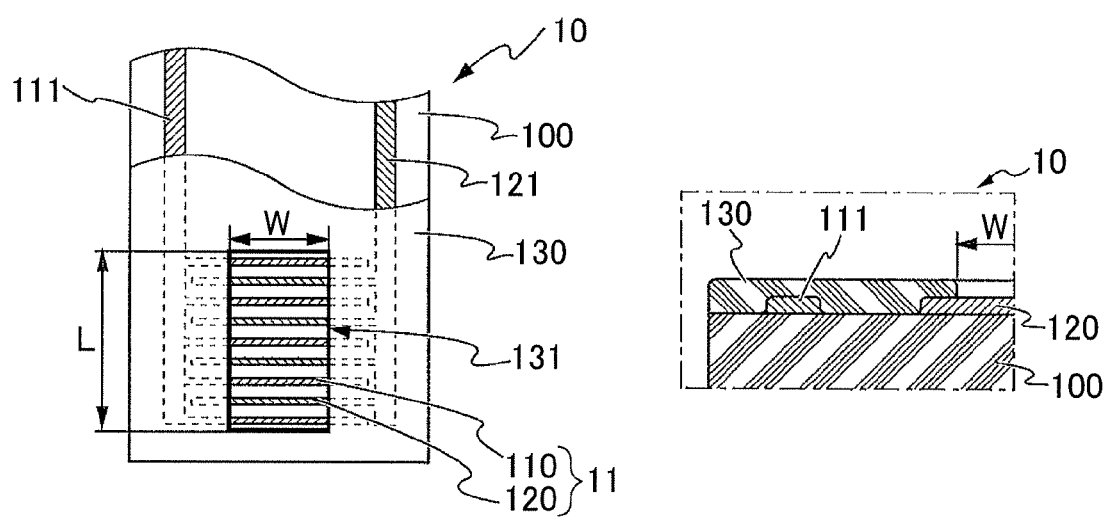
FIG. 1B is a plan view showing a main part of the PM detection element according to the first exemplary embodiment of the present invention.
FIG. 1C is a cross section of the main part of the PM detection element according to the first exemplary embodiment of the present invention.

FIG. 1A is a development view showing a perspective structure of the PM detection element 10 according to the first exemplary embodiment. FIG. 1B is a plan view showing a main part of the PM detection element 10 according to the first exemplary embodiment. FIG. 1C is a cross section of the main part of the PM detection element 10 according to the first exemplary embodiment.

The PM detection element 10 according to the first exemplary embodiment can be applied to exhaust gas purifying systems for internal combustion engines. The PM detection element 10 detects electrical characteristics such as electrical resistance and capacitance of a detection part 11 placed in target detection gas such as exhaust gas emitted from an internal combustion engine. The electric characteristics of the detection part 11 are changed according to the change of a quantity of particulate matter (PM) contained in the exhaust gas and accumulated on the area between electrodes of the detection part 11. The PM detection element 10 detects a quantity of PM contained in the target detection gas such as exhaust gas on the basis of the electrical characteristics of the detection part 11. Specifically, the PM detection sensor 11 is placed at a downstream of a diesel particulate filter (DPF) in order to detect abnormal state of the DPF. It is also possible to place the PM detection sensor 11 at an upstream of the DPF in order to directly detect the PM introduced into the DPF.

The structure of the PM detection element 10 according to the present invention exposes the target detection gas such as exhaust gas directly to the area having a uniform electric field intensity in the detection part 11. This makes it possible to prevent the non-uniform distribution of accumulated PM from being generated on the detection part 11. It is therefore possible for the PM detection element to have a stable dead time period (mass) and to detect PM contained in the target detection gas with high reliability.

A description will now be given of the PM detection element 10 according to the first exemplary embodiment of the present invention with reference to FIG. 1A, FIG. 1B and FIG. 1C.

FIG. 1A shows the PM detection element 10 in which a detection part 11, a protection layer 13 and a heater unit 14 are laminated and assembled together.

The detection part 11 is comprised of an insulation substrate 100 of an approximate flat plate, and a pair of detection electrodes 110 and 120 formed on the insulation substrate 100.

The insulation substrate 100 of an approximate flat shape is made of heat insulating material such as oxide ceramics and non-oxide ceramics by using known method such as doctor blade method. For example, there are alumina, titanium, zirconium, and spinel as oxide ceramics, and there are silicon nitride, aluminum nitride, and silicon carbide as non-oxide ceramics.

The detection electrodes 110 and 120 are made of conductive material such as platinum Pt and formed on the insulation substrate 100 by using known method such as thick-film printing method, plating, and vapor deposition method.

In the structure of the PM detection element 10 according to the first exemplary embodiment, the detection electrodes 110 and 120 is connected to detection electrode lead parts 111 and 121, respectively. The detection electrode lead parts 111 and 121 are connected to an external detection circuit (not shown) through corresponding detection electrode terminals 112 and 122, respectively. Electrodes of the detection electrodes 110 and 120 are alternately arranged in a comb structure. The electrodes of the detection electrodes 110 and 120 are formed in a direction which is perpendicular to the longitudinal direction of the detection electrode lead parts 111 and 121.

The adjacent electrodes of the detection electrodes 110 and 120 alternately face to each other.

The protection layer 13 is stacked on the surface of the detection part 11. The protection layer 13 is comprised of a non-uniform electric field intensity area shielding layer 130, a shielding layer opening part 131, and an insulation protection layer 132. The insulation protection layer 132 insulates the detection electrode lead parts 111 and 121 from each other.

The non-uniform electric field intensity area shielding layer 130 covers a part of the detection part 11 as a shielding layer formation area.

The non-uniform electric field intensity area shielding layer 130 has an approximate flat shape and is made of heat insulating material such as oxide ceramics, non-oxide ceramics and heat insulating material by using known method such as doctor blade method, thick-film printing method, cold isostatic pressing (CIP), hot isostatic pressing (HIP), etc. For example, there are alumina, titanium, zirconium, and spinel as oxide ceramics, and are silicon nitride, aluminum nitride, and silicon carbide as non-oxide ceramics, and there is heat resistant glass as heat insulating material. The non-uniform electric field intensity area shielding layer 130 shields the area having non-uniform electric field intensity from the target detection gas such as exhaust gas.

The detection electrodes 110 and 120 are made of conductive material such as platinum Pt and formed on the insulation substrate 100 by using a known method such as thick-film printing method, plating, and vapor deposition method.

Specifically, the shielding layer formation area is the area which contains the front part of each of the detection electrodes 110 and 120, the connection part between the detection electrode and the corresponding detection electrode lead, and the area having electric field lines which are approximately parallel to the longitudinal side part of the detection electrodes 110 and 120. The electric field lines generated in the area between the adjacent detection electrodes 110 and 120 where the adjacent detection electrodes 110 and 120 face to each other have uniform electric field intensity.

Further, the shielding layer formation area contains the area in which an angle of an equipotential line of the electric field generated between the detection electrodes 110 and 120 to a reference line formed along the longitudinal edge of the detection electrodes 110 and 120 exceeds ±3°.

More specifically, for example, when the width of each of detection electrodes 110 and 120 is 150 μm, and the width of each of the detection electrode lead parts 111 and 121 is 150 μm, and the distance D between the adjacent detection electrodes 110 and 120 is 50 μm, and the distance between the front edge of one detection electrode 110 or 120 and the side edge of the other detection electrode 120 or 110 is 50 μm, it is preferable that the area which is covered with the non-uniform electric field intensity area shielding layer 130 is separated from the front edge of the detection electrodes 110 and 120 by at least 50 μm. That is, the area has the same distance D measured from the front edge of one detection electrode 110 or 120 to the side edge of the detection electrode lead part corresponding to the other detection electrode 120 or 110, that is, at least separated by 50 μm, or more than 200 μm when the detection electrode lead part is contained.

Still further, it is possible to cover a part of each of the detection electrodes 110 and 120 by approximately a thickness of 5 μm, measured from the front edge of each of the detection electrodes 110 and 120.

The shielding layer opening part 131 is formed in the non-uniform electric field intensity area shielding layer 130. Through the shielding layer opening part 131, the area having the uniform electric field intensity generated in the detection part 11 is exposed directly to the target detection gas such as exhaust gas. That is, the non-uniform electric field intensity area shielding layer 130 shields the area in the detection part 11 having non-uniform electric field intensity from the target detection gas such as exhaust gas.

Accordingly, the area in which the straight-line parts of a plurality of electrodes in the detection electrodes 110 and 120 arranged in parallel are exposed to the target detection gas such as exhaust gas through the shielding layer opening part 131 indicated by a predetermined opening width W and a predetermined opening length L shown in FIG. 1B. The shielding layer opening part 131 is designated by the solid line shown in FIG. 1B.

Further, in the shielding layer formation area shown in FIG. 1C, the surfaces of the detection electrodes 110 and 120 are covered with the non-uniform electric field intensity area shielding layer 130. In addition to this, the area between the detection electrodes 110 and 120 is covered with the non-uniform electric field intensity area shield layer 130. This makes it possible to insulate the front part of the detection electrode 100 from the detection electrode lead part 121, and to insulate the front part of the detection electrode 120 from the detection electrode lead part 111.

The heater unit 14 is stacked on the back surface of the insulation substrate 100 in which the detection part 11 is formed. The heater part 14 is comprised of a heating body 140, a pair of heating body lead parts 141a and 141b, a pair of through holes 142a and 142b and a pair of heating body terminals 143a and 143b. The heating body 140 is formed on the surface of or in the heating unit 14. The heating body 140 is connected to an external electric power supply control device (not shown) through the pair of the heating body lead parts 141a and 141b.

The heating body 140 is made of conductive ceramics such as Pt, W, $MoSi_2$, WC, etc. which generates heat energy when receiving electric power.

The heating body 140 is formed by using known method such as doctor blade method, CIP method, HIP method, thick-film printing method, etc.

A description will now be given of the operating principle of the PM detection element 10 according to the present invention with reference to FIG. 2 to FIG. 4.

Figure 2:
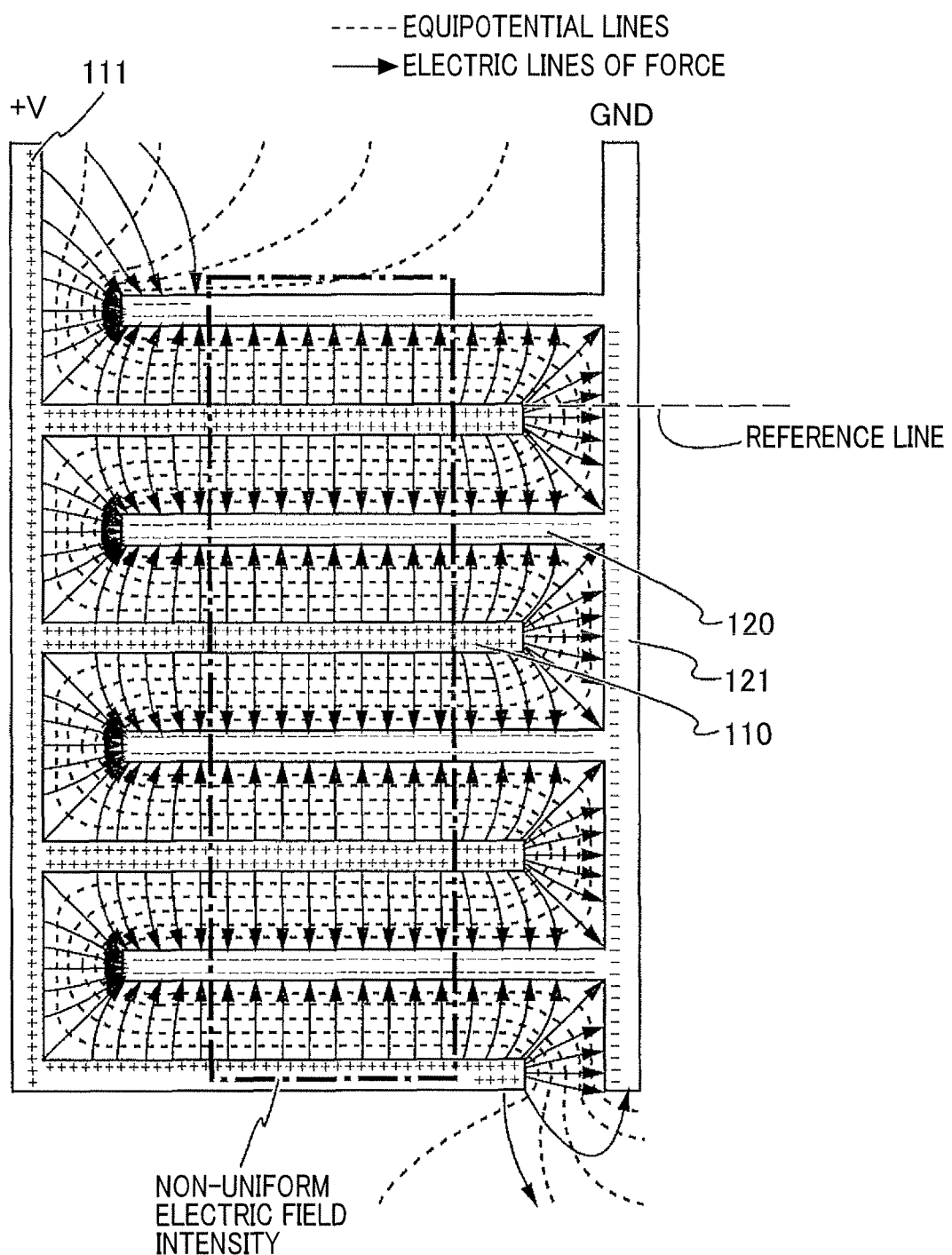
FIG. 2 is a schematic view showing equipotential lines and electric lines of force in the detection part of the PM detection element according to the first exemplary embodiment of the present invention.

FIG. 2 is a schematic view showing equipotential lines and electric lines of force in the detection part of the PM detection element 10 according to the first exemplary embodiment.

In the PM detection element 10, the detection electrode 110 is a positive electrode, and the detection electrode 120 is a ground electrode. When a voltage +V (for example, 30V) is supplied between the detection electrodes 110 and 120, the electric field is generated between the detection electrodes 110 and 120.

As shown in FIG. 2, in the area where the longitudinal parts of the detection electrodes 110 and 120 are arranged in parallel to each other and face together, the electric potential is changed so that equipotential lines are approximately parallel to the reference lines, and the electric lines of force are extended in a direction which is approximately perpendicular to the direction from the detection electrode 110 to the detection electrode 120.

However, the front part of one detection electrode 110 or 120 is surrounded by the bottom part of the other detection electrode 120 or 110 and the corresponding detection electrode lead part 121 or 111. This makes it possible to bend the equipotential lines generated between the front part of one detection electrode and the other detection electrode and the corresponding detection electrode lead part, and to expand the electric lines of force in a fan shape or to converge the electric lines of force into a fan shape.

Figure 3:
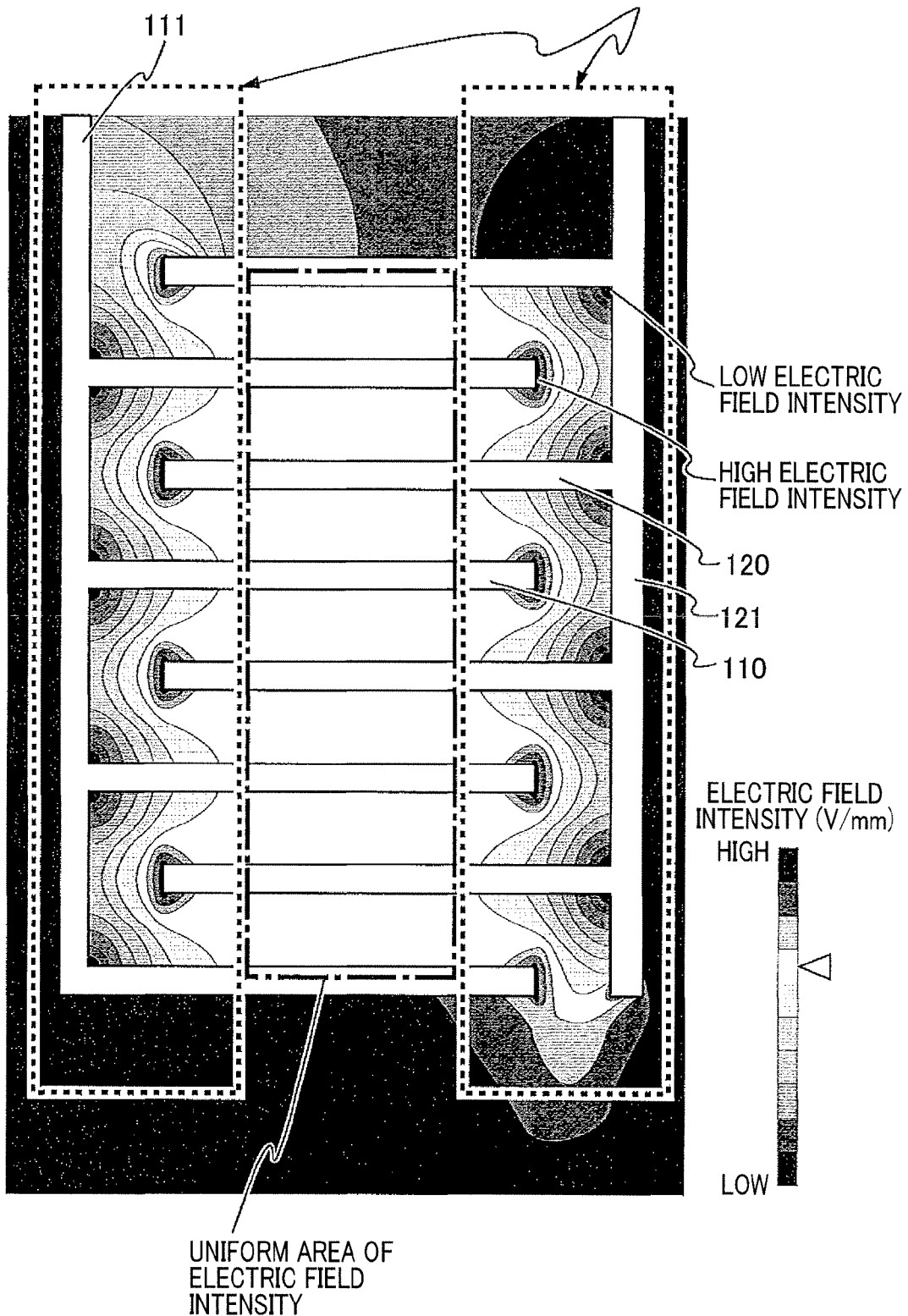
FIG. 3 is a schematic view showing a distribution of electric field intensity generated between the detection electrodes in the PM detection element according to the first exemplary embodiment of the present invention.

FIG. 3 is a schematic view showing a distribution of electric field intensity generated between the detection electrodes 110 and 120 in the PM detection element 10 according to the first exemplary embodiment. As shown in FIG. 3, electric field is concentrated at the front part of the detection electrodes 110 and 120, the electric field intensity around the front part thereof is increased. On the other hand, the electric field intensity at the bottom part of each of the detection electrodes 110 and 120, which is connected to the corresponding detection electrode lead part 111 and 121 is decreased.

As shown in FIG. 3, the area having the uniform electric field intensity is limited within a constant area in which the longitudinal part of the detection electrodes 110 and 120 face to each other. Further, it can be understood that an area having non-uniform electric field intensity is formed around the front part of the detection electrodes 110 and 120.

In the structure of the PM detection element 10 according to the present invention, the shielding layer formation area is formed on the area having the non-uniform electric field intensity. That is, the area having the non-uniform electric field intensity is covered with the non-uniform electric field intensity area shielding layer 130 made of heat insulating material.

FIG. 2 and FIG. 3 show simulation results of equipotential lines and electric lines of force around the detection part 11 and the detection electrode lead parts 111 and 121 when the two-dimensional Laplace's equation ($\partial^2 U/\partial x^2 + \partial^2 U/\partial y^2 = 0$) was solved by the difference method.

Figure 4:
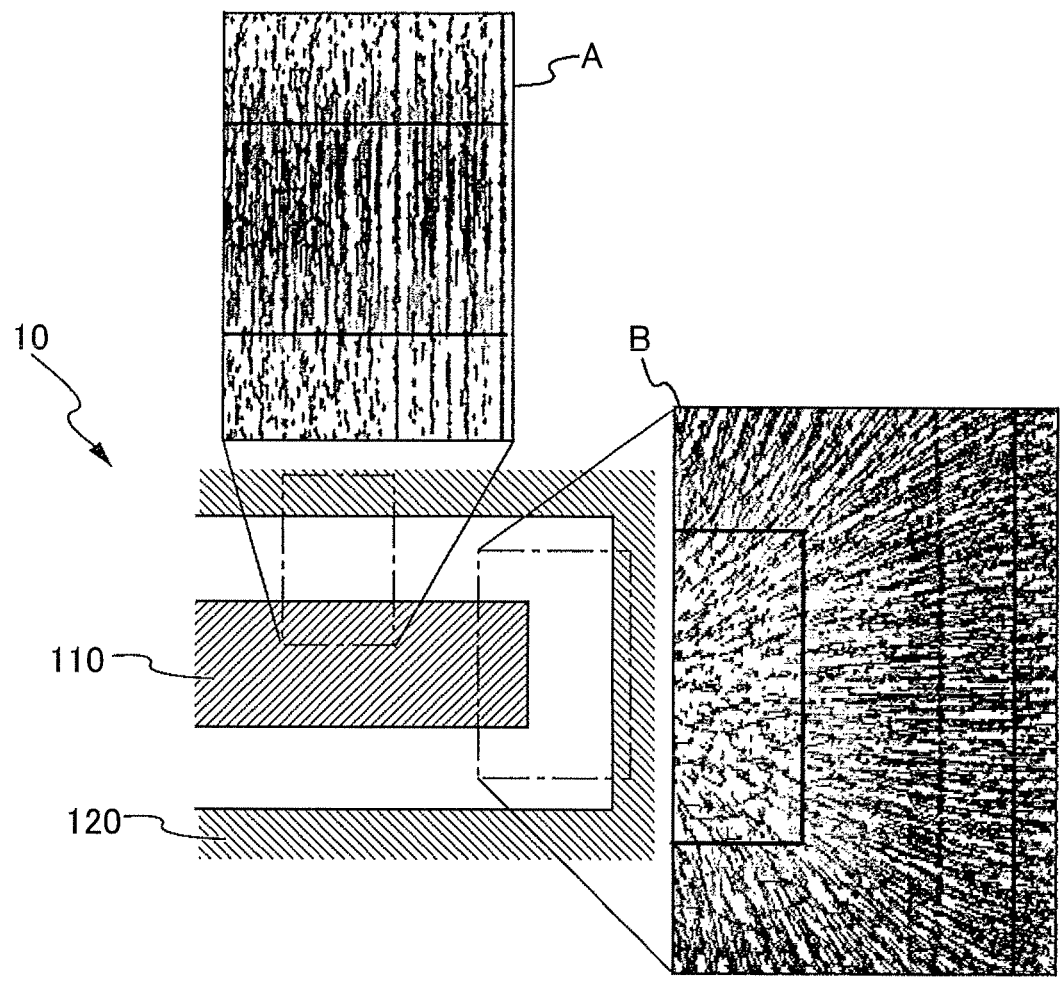
FIG. 4 is a view showing results of analyzing electric field, by finite element solution, generated between the detection electrodes of the PM detection element shown in FIG. 1.

FIG. 4 is a view showing results of analyzing electric field, by finite element solution, generated between the detection electrodes 110 and 120 of the PM detection element 10 shown in FIG. 1. As shown in FIG. 4, the area in which the longitudinal parts of the detection electrodes 110 and 120 face to each other, as designated by reference character A, the uniform electric field is generated, and the electric field vectors are formed in a direction which is approximately perpendicular to the longitudinal direction of the detection electrodes 110 and 120.

On the other hand, as designated by reference character B shown in FIG. 4, the electric field vectors are expanded in a radial pattern in the area surrounded by the front part of the detection electrode 110 and the detection electrode 120 and the detection electrode lead part 121.

Figure 5A:
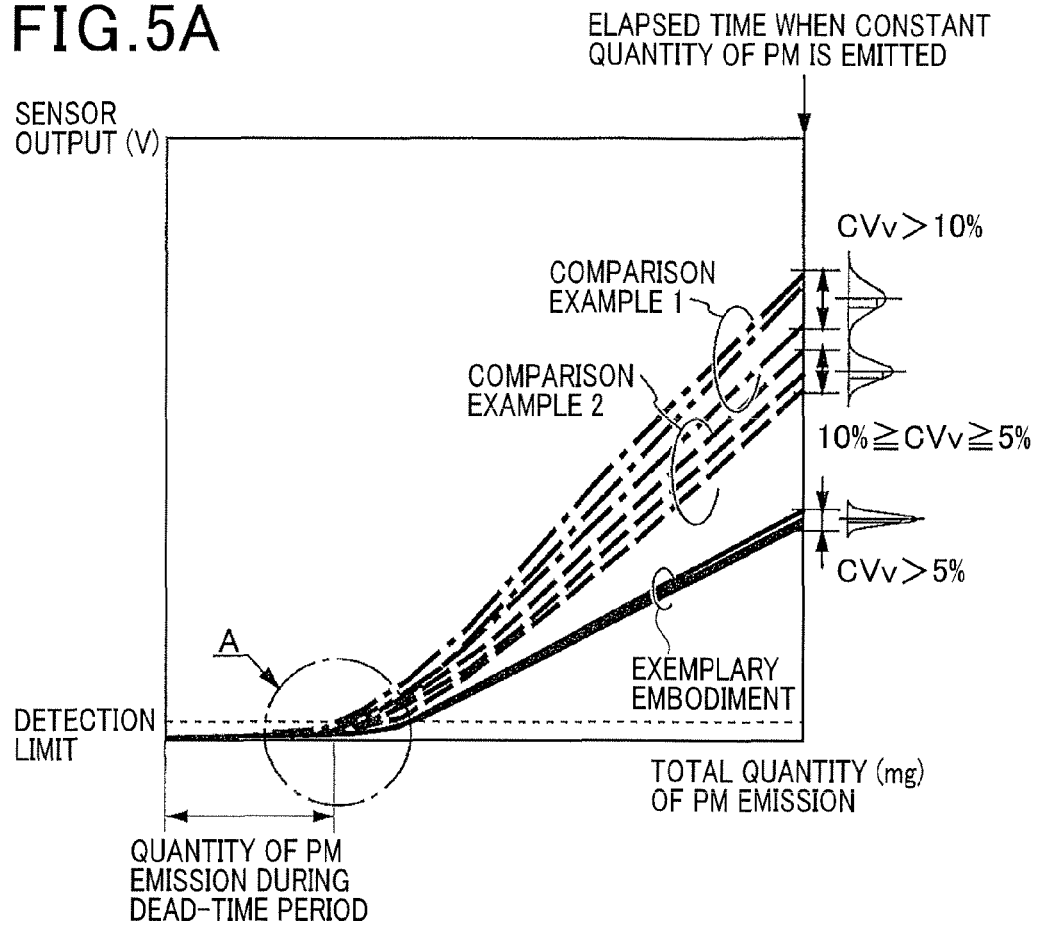
FIG. 5A is a view showing a change with passage of time of the characteristics of a sensor output of the PM detection element and comparison samples.
Figure 5B:
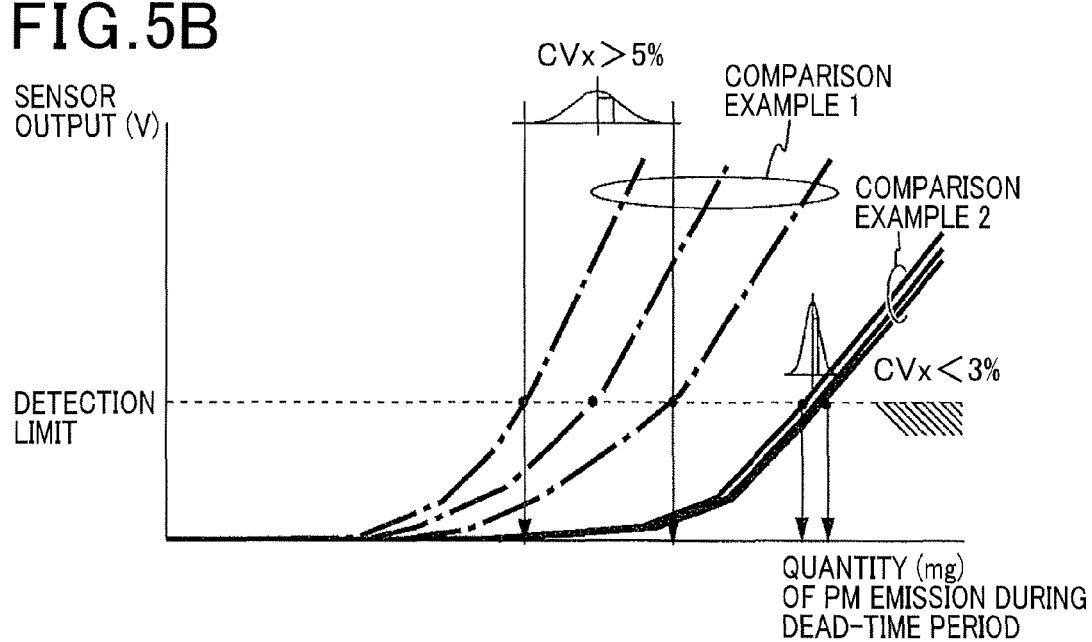
FIG. 5B is an enlarged view along the circle A shown in FIG. 5A.

FIG. 5A is a view showing a change with passage of time of the characteristics of a sensor output of the PM detection element 10 and comparison samples. FIG. 5B is an enlarged view along the circle A shown in FIG. 5A.

The comparison sample 1 does not have the non-uniform electric field intensity area shielding layer 130.

The comparison sample 2 is a PM detection element in which the shielding layer formation area contains the area in which an angle of an equipotential line of the electric field generated between the detection electrodes 110 and 120 exceeds 7° in absolute magnitude (±7°) to a reference line along the longitudinal edge of the detection electrodes 110 and 120.

The PM detection element according to the first exemplary embodiment of the present invention has the shielding layer formation area which contains the area in which an angle of an equipotential line of the electric field generated between the detection electrodes 110 and 120 to a reference line along the longitudinal edge of the detection electrodes 110 and 120 exceeds 3° in absolute magnitude.

An automotive test system was used as the evaluation environment to evaluate the functions of each of the PM detection element 10 according to the first exemplary embodiment of present invention and the comparison samples 1 and 2.

In usual driving of a motor vehicle, the PM detection element according to the present invention and the PM detection elements as the comparison samples were placed at the position by 120 cm measured from oxidation catalyst. In the evaluation test, PM concentration in target detection gas was 0.4 mg/s. The change with passage of time of the electrical characteristics of the sensor output of the PM detection element and comparison samples was detected. FIG. 5A and FIG. 5B show the detection results. In FIG. 5A and FIG. 5B, the horizontal axis indicates a total quantity (mg) of PM emission, and a vertical axis indicates the sensor output (V).

The experiment calculated the quantity of PM accumulated in each of the comparison samples 1 and 2 and the embodiment 1 during a dead time period. The dead time period is counted from the detection start time to the time when the sensor output exceeds 0.01 V as the minimum detection value, namely, the detection limit.

Further, the experiment further calculated an average value (X bar) and a standard deviation ($\sigma_x$) of the calculated quantity of the accumulated PM during the dead time period. The experiment calculated a detection fluctuation CVx ($=\sigma_x/V$ Bar×100) (%) of the detected PM quantity during the dead time period. Still further, the experiment calculates the average value (V bar) and a standard deviation ($\sigma_v$) during a constant emission period in which PM of a constant quantity is emitted from the automotive test system. The experiment calculated a sensor output fluctuation CVv ($=\sigma_v/V$ Bar×100) (%) during the constant PM emission period.

Table 1 shows the above detection and calculation results.

TABLE 1

| | Shielding layer Formation range | CVx | CVv | Results |
|---|---|---|---|---|
| Comparison Sample 1 | Without shielding layer | .7% | >10% | x |
| Comparison Sample 2 | With shielding layer within >7° and <7° | 3%~5% | 5%~10% | ○ |
| Exemplary embodiment of the present invention | With shielding layer within >3° and <3° | 3%> | 5%> | □ |

As shown in Table 1 and FIG. 5A and FIG. 5B, the comparison sample 1 has the detection fluctuation CVx of not less than 5% during the dead time period, and the detection fluctuation CVx of not less than 10% during the constant emission period. As a result, the comparison sample 1 has the detection result designated by reference character "x". That is, the comparison sample 1 does not have any improved function.

On the other hand, the comparison sample 2 has the detection fluctuation CVx ($=\sigma_x/V$ Bar×100) (%) within a range of 3% to 5% of the detected PM quantity during the dead time period, which is slightly improved when compared with that of the comparison sample 1.

Further, the comparison sample 2 has the sensor output fluctuation CVv ($=\sigma_v/V$ Bar×100) (%) within a range of 5% to 10% during the constant PM emission period, which is slightly improved when compared with that of the comparison sample 1, and designated by reference character "○" in table 1.

On the other hand, the first exemplary embodiment has the detection fluctuation CVx ($=\sigma_x/V$ Bar×100) (%) of not more than 3% of the detected PM quantity during the dead time period, and has the sensor output fluctuation CVv ($=\sigma_v/V$ Bar×100) (%) of not more than 5% during the constant PM emission period, as designated by reference character "□" shown in Table 1.

As shown in Table 1, the first exemplary embodiment has the superior characteristics when compared with that of each of the comparison samples 1 and 2.

A description will now be given of the results of analyzing the distribution of electric field in the PM detection element 10 and a modification thereof with reference to FIG. 6A to FIG. 6F.

FIG. 6A to FIG. 6F shows distributions of electric field intensity of various types of PM detection elements.

In FIG. 6A to FIG. 6F, reference character "A" indicates the electric field level in the uniform electric field intensity in the PM detection elements and the modifications thereof according to the first exemplary embodiment.

Figure 6A:
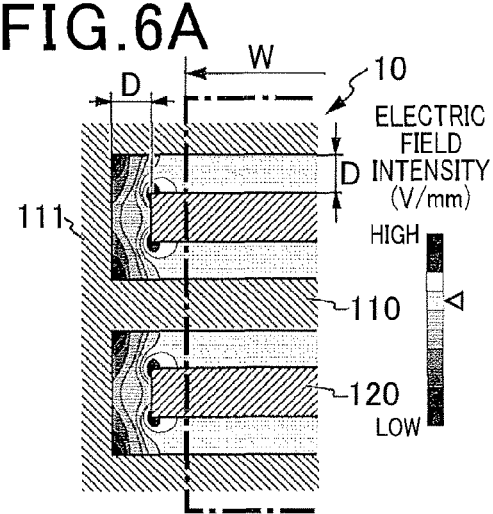
FIG. 6A to FIG. 6F show distributions of electric field intensity of various types of PM detection elements.

When the gap between the longitudinal part of the detection electrode 10 and the longitudinal part of the detection electrode 120 in the PM detection element 10 is D, and the gap between the front part of the detection electrode 110 or 120 to the detection electrode 120 or 110 is D, as shown in FIG. 6A, the area around the front part of the detection electrode 110 or 120 has non-uniform electric field. The longitudinal part having the length W of each of the detection electrodes 110 and 120 is uniform.

Figure 6D:
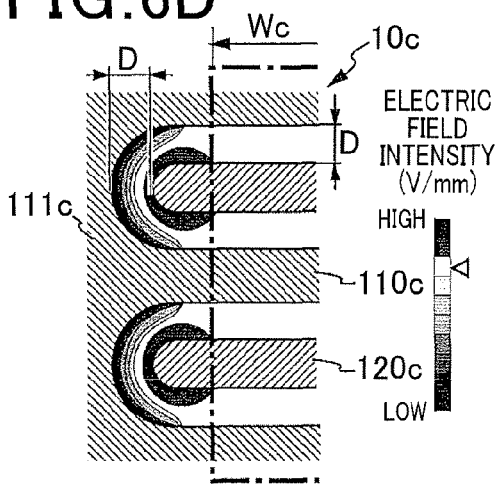
Figure 6B:
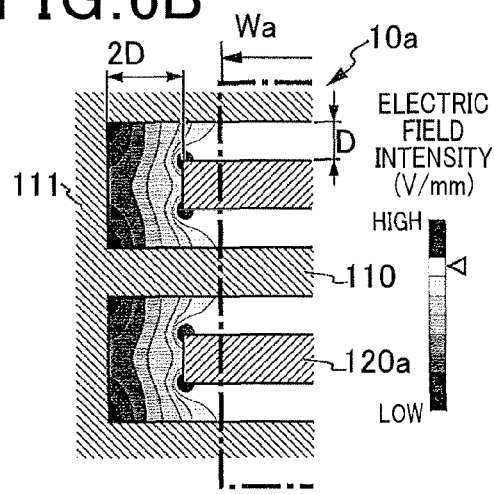
Figure 6E:
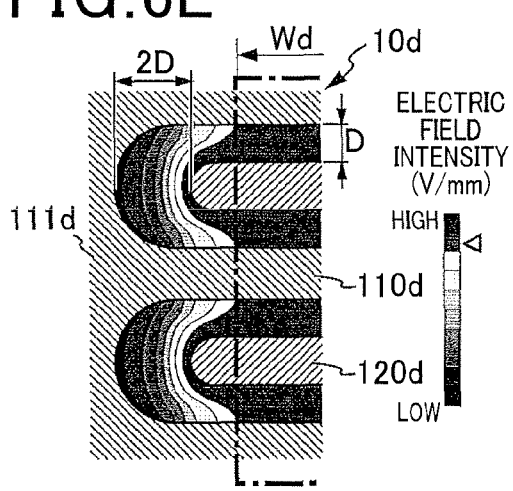

The modification 10a of the PM detection electrode 10 shown in FIG. 6B has the distance, measured from the front part of each of the detection electrodes 110a and 120a to the corresponding detection electrode lead part 111, 121, is twice of the gap D between the longitudinal parts of the adjacent detection electrodes 110 and 120.

Although the area Wa having the uniform electric field intensity in the longitudinal part is narrow than that of the PM detection sensor 10 shown in FIG. 6A, it is possible to increase the electric field intensity in the uniform electric field area Wa rather than the case shown in FIG. 6A because this structure suppresses the concentration of the electric field at the front part of each of the detection electrodes 110 and 120.

However, it is possible for the PM detection element according to the first exemplary embodiment to suppress the detection fluctuation of the detected PM quantity during the dead time period, to increase the PM accumulation speed, and to further decrease the dead time period.

Figure 6C:
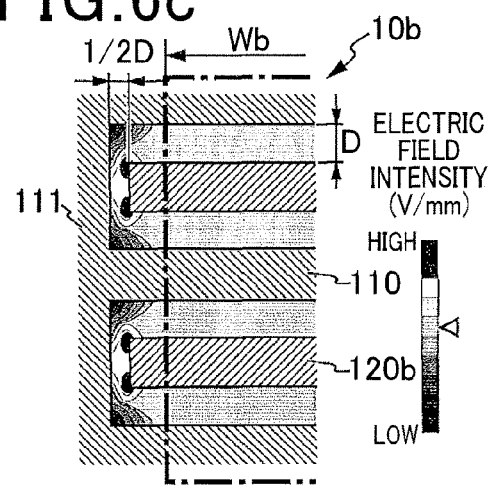
Figure 6F:
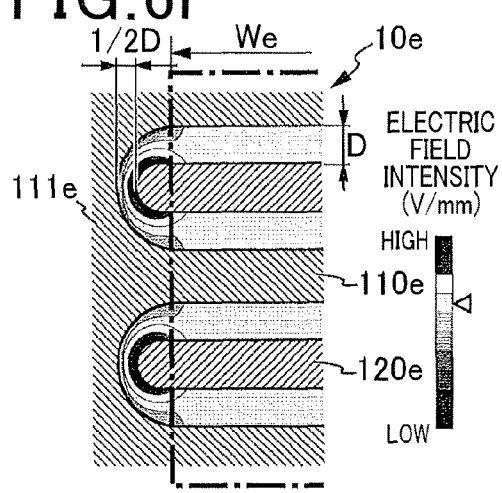

Other modification shown in FIG. 6C has the distance, counted from the front part of each of the detection electrodes 110a and 120a to the corresponding detection electrode lead part 111, 121, is half of the gap D between the longitudinal parts of the adjacent detection electrodes 110 and 120.

In this structure, the electric field intensity around the front part of each of the detection electrodes 110b and 120b is further increased, and the electric field intensity at the area Wb having the uniform electric field intensity in the longitudinal part is relatively decreased.

However, no short circuit is made between the front part of each of the detection electrodes 110a and 120a because the front part of each of the detection electrodes 110a and 120a is electrically insulated by the non-uniform electric field intensity area shielding layer 130.

Further, it is possible to prevent PM from being locally accumulated in the area having a high electric field intensity because this area is covered with the non-uniform electric field intensity area shielding layer 130. It is therefore possible for the area having the high electric field intensity to have the same effects of the PM detection element 10 previously described.

Further, in the structure of the example shown in FIG. 6C, because the area Wb having the uniform electric field intensity becomes wide when compared with that of the structure shown in FIG. 6A, and the electric field intensity in the area Wb having the uniform electric field intensity is decreased, it is possible to prolong the period of time until the next execution of the regeneration process.

In the structure of the modification shown in FIG. 10c shown in FIG. 6D, the front part of each of the detection electrodes 110c and 120c has a rounded shape or a curved shape. This structure shown in FIG. 6D makes it possible to suppress the concentration of the electric field and to further increase the electric field intensity in the area We having the uniform electric field intensity when compared with that of the structure shown in FIG. 6C. This structure shown in FIG. 6D makes it possible to have the same effects of the PM detection element 10 and to further prolong the period of time until the next execution of the regeneration process.

Further, in the structure of the modification 10d shown in FIG. 10E, the distance measured from the front part of each of the detection electrodes 110d and 120d to the corresponding detection electrode lead part 111d and 121d is twice of the gap D between the adjacent longitudinal part of the detection electrodes 110d and 120d in addition to the structure in which each of the front part of each of the detection electrodes 110d and 120d and the bottom part of each of the detection electrodes 110d and 120d connected to the corresponding detection electrode lead part 111d and 121d has the rounded shape.

This structure makes it possible to further increase the electric field in the area Wd having the uniform electric field intensity. Further, this structure shown in FIG. 6E makes it possible to have the same effects of the PM detection element 10 and to further prolong the period available to execute the regeneration process.

Still further, in the structure of the modification 10e shown in FIG. 10F, the distance measured from the front part of each of the detection electrodes 110e and 120e to the corresponding detection electrode lead part 111e and 121e is half of the gap D between the adjacent longitudinal part of the detection electrodes 110e and 120e in addition to the structure in which each of the front part of each of the detection electrodes 110e and 120e and the bottom part of each of the detection electrodes 110e and 120e connected to the corresponding detection electrode lead part 111e and 121e has the rounded shape.

Because this structure makes it possible to avoid the increasing of electric field intensity in the area We having the uniform electric field intensity generated by the structure of the rounded shape and to cancel the decreasing of electric field intensity in the area We generated by decreasing the distance between the front part and the detection electrode lead part.

This structure makes it possible to further have the same electric field in the structure shown in FIG. 6A and to expand the area We having the uniform electric field intensity. This structure shown in FIG. 6E makes it possible to have the same effects of the PM detection element 10 shown in FIG. 6A and to further prolong the period available to execute the regeneration process.

Still further, according to the PM detection element according to the present invention, because the non-uniform electric field intensity area shielding layer 130 is generated between the front part of each of the detection electrodes and the corresponding detection electrode lead part, it is possible to prevent a short circuit from being generated even if a high voltage is supplied between the detection electrodes. This makes it possible to provide the PM detection element having high reliability.

On the other hand, in a conventional structure in which the area between a front part of a detection electrodes and a corresponding detection electrode lead part is exposed to target detection gas, a short circuit is made by concentrating electric field the above area and PM is locally accumulated on the area having the concentrated electric field unless the area has the same gap between the longitudinal parts of the adjacent detection electrodes when a high voltage is supplied between the detection electrodes. This conventional structure cannot suppress the fluctuation of the length of the dead time period.

Further, in the structure of the PM detection element according to the present invention, it is possible to suppress the fluctuation of the dead time period regardless of the shape of the cover unit which protects the PM detection element. It is therefore possible for the PM detection element according to the present invention to stably accumulate PM on the detection part, and as previously described, to adjust the magnitude of electric field intensity in the area having the uniform electric field intensity by adjusting the distance between the front part of the detection electrode and the corresponding detection electrode lead part and by adjusting the shape of the front part and the bottom part of each of the detection electrodes. The present invention provides the flexible PM detection element.

Second Exemplary Embodiment

A description will be given of a particulate matter detection element 10f (hereinafter, referred to as the "PM detection element 10f") according to a second exemplary embodiment of the present invention with reference to FIG. 7A, FIG. 7B, FIG. 8A and FIG. 8B.

Figure 7A:
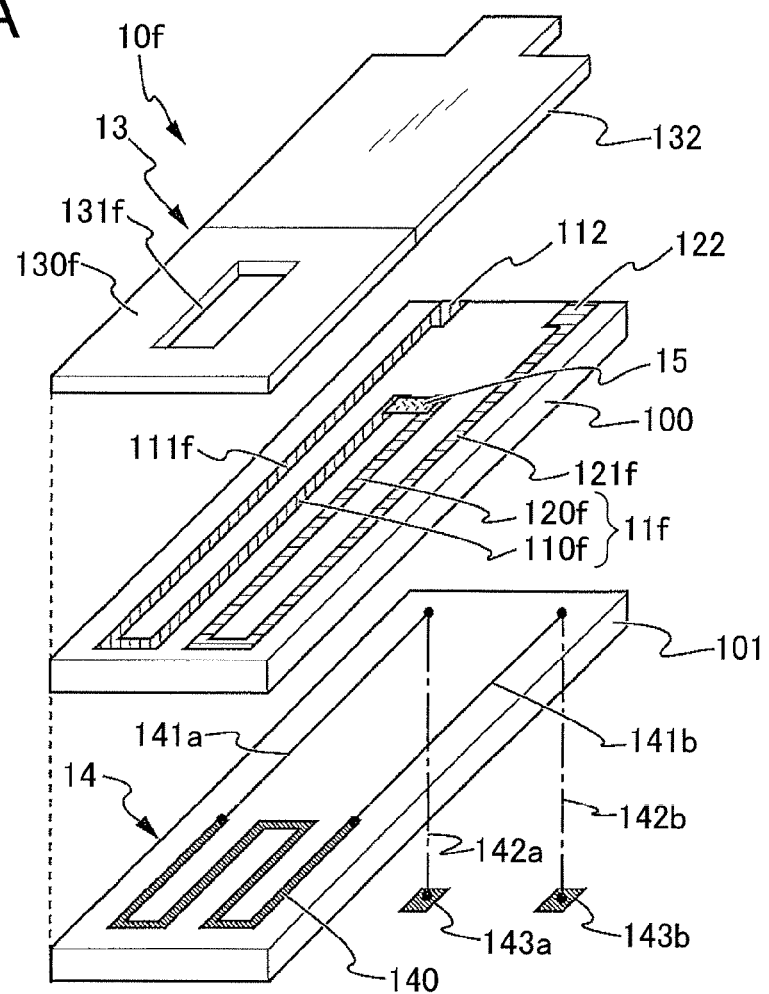
FIG. 7A is a development view showing a perspective structure of a PM detection sensor according to a second exemplary embodiment of the present invention.
Figure 7B:
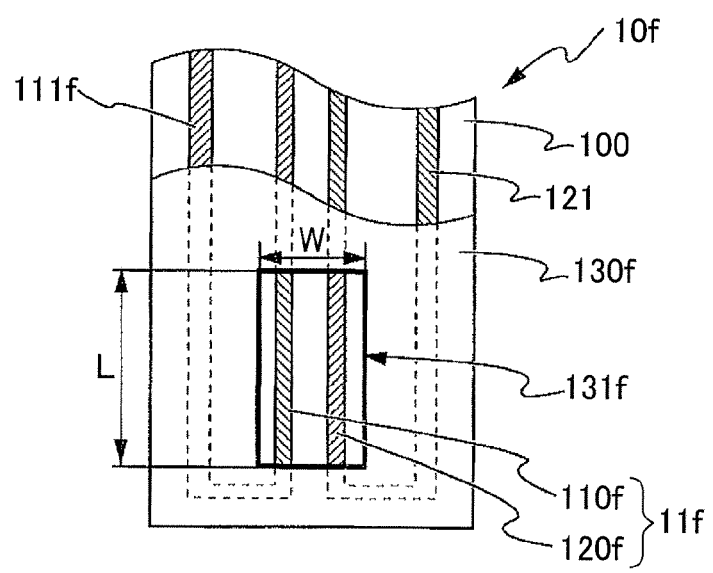
FIG. 7B is a plan view showing a main part of the PM detection sensor according to the second exemplary embodiment of the present invention shown in FIG. 7A.

FIG. 7A is a development view showing a perspective structure of the PM detection sensor 10f according to the second exemplary embodiment of the present invention. FIG. 7B is a plan view showing a main part of the PM detection sensor 10f according to the second exemplary embodiment shown in FIG. 7A.

The same components of the PM detection sensor 10f according to the second embodiment and the PM detection sensor 10 according to the first embodiment will be referred to with the same reference numbers and characters. The explanation of the same components is omitted here.

In the PM detection sensor 10 according to the first exemplary embodiment previously described has the structure in which the detection electrodes 110 and 120 have a plurality of electrodes parts alternately arranged in a comb structure. The concept of the present invention is not limited by the structure of the first embodiment. It is possible for the PM detection sensor 10f to have a detection part 11f in which a pair of detection electrodes 110f and 120f is formed in parallel along the longitudinal direction of the PM detection sensor 10f.

As shown in FIG. 7A and FIG. 7B, the bent part of each of the detection electrodes 110f and 120f is covered with an non-uniform electric field intensity area shielding layer 130f because it is easy to concentrate the electric field at the bent part of each of the detection electrodes 110f and 120f. This structure makes it possible to provide the uniform electric field intensity generated in the inside of a shielding layer opening part 131 (see FIG. 7B).

The one end part of each of the detection electrodes 110f and 120f is connected to a corresponding detection electrode lead part 111f and 121f. The detection electrode lead parts 111 and 121 are connected to an external detection circuit. The other end part of each of the detection electrodes 110*f* and 120*f* are connected together through a passive element 15. That is, the passive element 15 is formed between the other end part of each of the detection electrodes 110*f* and 120*f* so that the passive element 15 connects the detection electrodes 110*f* and 120*f* together in series.

It is possible to use, as the passive element 15, one of a resistance element having a predetermined resistance and a capacitance element having a predetermined capacitance.

When the capacitor element is used as the passive element, a capacitance component is connected in parallel to the detection resistance formed by PM accumulated between the detection electrodes 110*f* and 120*f*. This case makes it possible to detect breaking of a wire which connects the PM detection sensor 10*f* to the external detection circuit (not shown) when an alternating current voltage is supplied between the detection electrodes 110*f* and 120*f*.

Further, when the resistance element is used as the passive element, because an electric resistance is connected in parallel to the detection resistance, the detection resistance is relatively decreased, and it is possible to decrease the dead time period. Further, because a conductive state is maintained even if no PM is accumulated on the detection part 11*f*, it is possible to detect breaking of a wire between the PM detection sensor 10*f* and the external detection circuit (not shown).

Figure 8A:
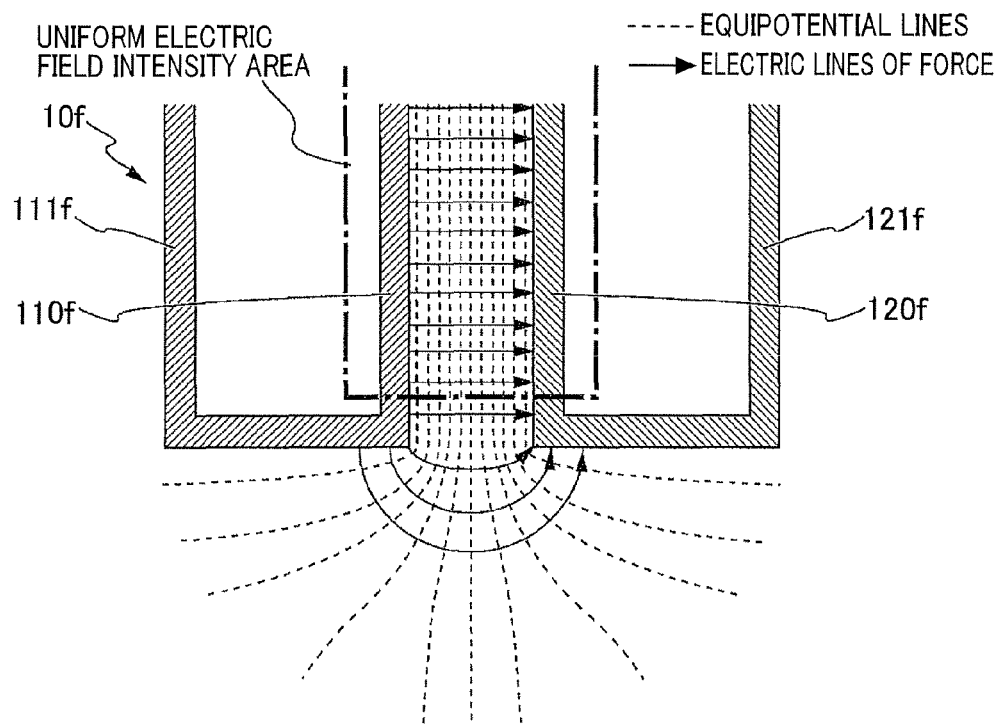
FIG. 8A is a schematic view showing equipotential lines and electric lines of force in the detection part of the PM detection element according to the second exemplary embodiment of the present invention shown in FIG. 7A and FIG. 7B.
Figure 8B:
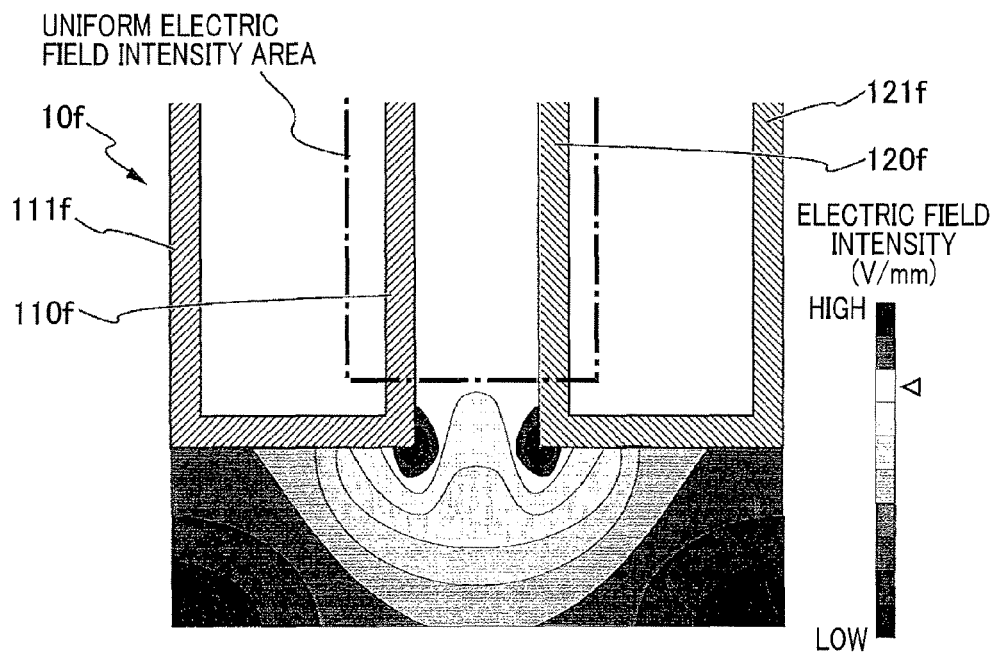
FIG. 8B is a view showing a distribution of electric field intensity in the detection electrodes of the PM detection element according to the second exemplary embodiment of the present invention shown in FIG. 7A and FIG. 7B.

FIG. 8A is a schematic view showing equipotential lines and electric lines of force in the detection part of the PM detection element 10*f* according to the second exemplary embodiment of the present invention shown in FIG. 7A and FIG. 7B. FIG. 8B is a view showing a distribution of electric field intensity in the detection electrodes of the PM detection element 10*f* according to the second exemplary embodiment of the present invention shown in FIG. 7A and FIG. 7B.

As shown in FIG. 8A and FIG. 8B, the structure of the PM detection sensor 10*f* according to the second exemplary embodiment makes it possible to uniform the electric field intensity in the shielding layer opening part 131*f*. Further, the structure of the PM detection sensor 10*f* makes it possible to suppress PM from being locally accumulated on the detection part 11*f*, and to prevent the fluctuation of the detection fluctuation of the detected PM quantity during the dead time period, and to suppress the fluctuation of the sensor output. That is, the second exemplary embodiment also provides the PM detection sensor 10*f* with high reliability.

Still further, it is possible to suppress the electric field from being locally concentrated on the detection part and to increase the electric field intensity between the detection electrodes 110*f* and 120*f* when each of the detection electrodes 110*f* and 120*f* has a bent part of a rounded shape which is connected to the corresponding detection electrode lead part 111*f* and 121*f*.

The first and second exemplary embodiments and the modifications thereof show the PM detection sensors capable of detecting the electric resistance as the electrical characteristics which are changed according to the quantity of PM accumulated on the detection part. The concept of the present invention is not limited by these embodiments. For example, it is acceptable to detect an electrostatic capacitance and impedance of the PM detection element instead of detecting the electric resistance. In this case, it is possible to suppress PM from being locally accumulated on the detection part and to increase the detection accuracy of the electrostatic capacitance and the element impedance as the detection target by forming the non-uniform electric field intensity area shielding layer 130 on the area having non-uniform electric field intensity formed between the detection electrodes.

While specific embodiments of the present invention have been described in detail, it will be appreciated by those skilled in the art that various modifications and alternatives to those details could be developed in light of the overall teachings of the disclosure. Accordingly, the particular arrangements disclosed are meant to be illustrative only and not limited to the scope of the present invention which is to be given the full breadth of the following claims and all equivalents thereof.

What is claimed is:

1. A particulate matter detection element capable of detecting particulate matter contained in a target detection gas, comprising:
   an insulation substrate;
   a detection part comprised of a pair of detection electrodes formed a predetermined distance apart on a surface of the insulation substrate; and
   a shielding layer made of heat insulating material which covers a predetermined area on the detection part so that an area having a uniform electric field intensity generated when a voltage is supplied between the detection electrodes is exposed to the target detection gas and an area other than the area having the uniform electric field intensity is shielded from the target detection gas;
   wherein the area other than the area having the uniform electric field intensity formed on the detection part does not include an area in which equipotential lines of the electric field generated when the voltage is supplied between the detection electrodes are approximately parallel to a reference line defined along a longitudinal part of each of the detection electrodes.

2. The particulate matter detection element according to claim 1 wherein in the area other than the area having the uniform electric field intensity, an angle of the equipotential line of the electric field to the reference line exceeds ±3°.

\* \* \* \* \*